US006124327A

United States Patent [19]
Silverman et al.

[11] Patent Number: 6,124,327
[45] Date of Patent: Sep. 26, 2000

[54] HIV INTEGRASE INHIBITORS

[75] Inventors: Keith C. Silverman, Somerset; Russell B. Lingham, Watchung; Sheo Bux Singh, Edison; Deborah L. Zink, Manalapan, all of N.J.; Ana Teran, Madrid, Spain

[73] Assignee: Merck & Co., Inc., Rahway, N.J.

[21] Appl. No.: 09/123,180

[22] Filed: Jul. 27, 1998

Related U.S. Application Data

[60] Provisional application No. 60/054,074, Jul. 29, 1997.

[51] Int. Cl.$^7$ .......................... C07C 69/84; A61K 31/235
[52] U.S. Cl. ............................. 514/352; 514/533; 560/70
[58] Field of Search .............................. 560/70; 514/532, 514/533

[56] References Cited

U.S. PATENT DOCUMENTS 5,759,842  6/1998  Dombrowski et al. ............... 435/252.1

FOREIGN PATENT DOCUMENTS 2 306 476A  5/1997  United Kingdom .
WO 96/28443  9/1996  WIPO .

OTHER PUBLICATIONS

LaFemina et al., Antimicrobial Agents & Chemotherapy, vol. 39(2), pp. 320–324 (1995), "Inhibition of human immunodeficiency virus integrase by bis–catechols".

Cushman et al., J. Med. Chem., vol. 38 (1995), pp.443–452, "Cosalane analogues with enhanced potencies as inhibitors of HIV–1 protease and integrase".

Mazumder et al., Biochemistry, vol. 34 (1995), pp. 15111–15122, "Effects of tyrphostins, protein kinase inhibitors, on human immunodeficiency virus type 1 integrase".

Mazumder et al., J. Med. Chem., vol. 39 (1996), pp 2472–2481, "Antiretroviral agents as inhibitors of both human immunodeficiency virus type 1 integrase and protease".

Mazumder et al., Molecular Pharmacology, vol. 49 (1996), pp. 621–628, "Effects of nucleotide analogues on human immunodeficiency virus type 1 integrase".

Zhao et al., J. Med. Chem., vol. 40 (1997), pp. 937–941, "Hydrazide–containing inhibitors of HIV–1 integrase".

Mazumder et al., AIDS Research and Human Retroviruses, vol. 11(1), pp. 115–125 (1995), "Inhibition of human immunodeficiency virus type 1 integrase by a hydrophobic cation . . . "

Mazumder et al., Proc. Nat'l Acad. Sci. USA, vol. 91, pp. 5771–5775 (1994), "Inhibition of human immunodeficiency virus type 1 integrase by 3'–azido–3'–deoxythymidylate".

Carteau et al., Archives of Biochemistry & Biophysics, vol. 305(2), pp. 606–610 (1993), "Inhibitory effect of the polyanionic drug suramin on the in vitro HIV DNA integration reaction".

Fesen et al., Proc. Nat'l Acad. Sci. USA, vol. 90 (1993), pp. 2399–2403, "Inhibitors of human immunodeficiency virus integrase".

Farnet et al., Proc. Nat'l Acad. Sci. USA, vol. 93 (1996), pp. 9742–9747, "Differential inhibition of HIV–1 preintegration complexes and purified integrase protein by small molecules".

Lutzke et al., Proc. Nat'l Acad. Sci. USA, vol. 92 (1995), pp. 11456–11460, "Identification of a hexapeptide inhibitor of the human immunodeficiency virus integrase protein by using a combinatorial chemical library".

Ojwang et al., Antimicrobial Agents & Chemotherapy, vol. 39(11), pp. 2426–2435 (1995), "T30177, an oligonucleotide stabilized by an intramolecular guanosine octet, is a potent inhibitor . . . "

Eich et al., J. Med. Chem., vol. 39 (1996), pp. 86–95, "(+)–Arctigenin as a lead structure for inhibitors of human immunodeficiency virus type–1 integrase".

Robinson, Jr., et al., Proc. Nat'l Acad. Sci. USA, vol. 93 (1996), pp. 6326–6331, "Inhibitors of HIV–1 replication that inhibit HIV integrase".

PRNewswire, Sep. 17, 1996, "Aronex reports results for lead anti–HIV integrase inhibitor compound".

Neamati et al., "Design and discovery of HIV–1 integrase inhibitors", DDT2(11) (1997), pp. 487–498.

Hazuda et al., Nucleic Acids Research, vol. 22 (6), pp. 1121–1122 (1994), "A novel assay for the DNA strand–transfer reaction of HIV–1 integrase".

Burke et al., J. Med. Chem., vol. 38 (1995), pp. 4171–4178, "Hydroxylated aromatic inhibitors of HIV–1 integrase".

Hazuda et al., J. of Virology, vol. 71(1), ppl 807–811 (1997), "Equivalent inhibition of half–site and full–site retroviral strand transfer reactions by structurally diverse compounds".

Fesen et al., Biochemical Pharma., vol. 48(3), pp. 595–608 (1994), "Inhibition of HIV–1 integrase by flavones, caffeic acid phenethyl ester (cape) and related compounds".

Zhao et al., J. Med. Chem., vol. 40 (1997), pp. 1186–1194, "Arylamide inhibitors of HIV–1 integrase".

*Primary Examiner*—Robert Gerstl
*Attorney, Agent, or Firm*—Catherine D. Fitch; Kenneth R. Walton; Melvin Winokur

[57] ABSTRACT

Natural products such as certain dimerized hydroxyphenylundecanes are described. These compounds are useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

14 Claims, No Drawings

HIV INTEGRASE INHIBITORS

CROSS-REFERENCE TO RELATED APPLICATIONS

The present invention is related to U.S. provisional application Serial No. 60/054,074, filed Jul. 29, 1997, the contents of which are hereby incorporated by reference.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid cells. Integration is believed to occur in three stages: cleavage of two nucleotides from the 3' termini of the linear proviral DNA; covalent joining of the recessed 3' OH termini of the proviral DNA at a staggered cut made at the host target site; repair synthesis by host enzymes.

Nucleotide sequencing of HIV shows the presence of a pol gene in one open reading frame [Ratner, L. et al., Nature, 313, 227 (1985)]. Amino acid sequence homology provides evidence that the pol sequence encodes reverse transcriptase, an integrase and an HIV protease [Toh, H. et al., EMBO J. 4, 1267 (1985). Power, M. D. et al., Science, 231, 1567 (1986); Pearl, L. H. et al., Nature 329, 351 (1987)].

It is known that some antiviral compounds act as inhibitors of HIV and are effective agents in the treatment of HIV and similar diseases, e.g., azidothymidine or AZT. Applicants demonstrate that the compounds of this invention are inhibitors of HIV integrase, probably by inhibiting strand transfer and cleavage activity. The particular advantage of the present invention is specific inhibition of HIV integrase.

Applicants have discovered that certain dimerized hydroxyphenylundecane derivatives are potent inhibitors of HIV integrase. These compounds are useful for the treatment of AIDS or HIV infection.

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

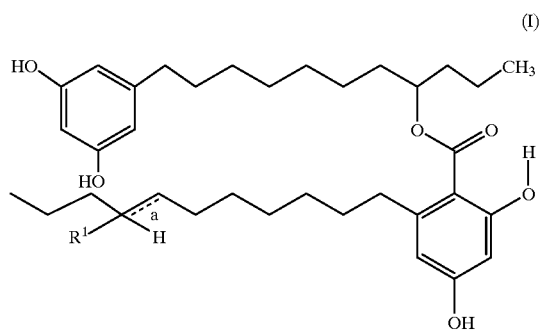

wherein:
when "a" represents a single bond, $R^1$ is selected from:
(1) —OH, and
(2) —OC(O)—CH$_3$; and
when "a" represents a double bond,
$R^1$ is absent,
and pharmaceutically acceptable salts and esters thereof.
Particular compounds of structural formula I include:

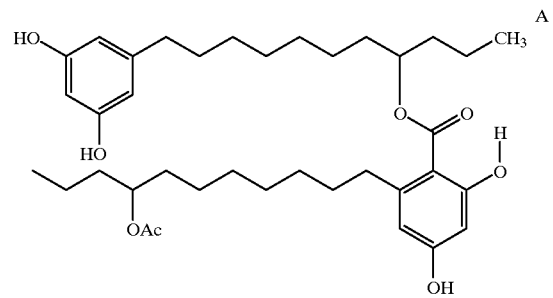

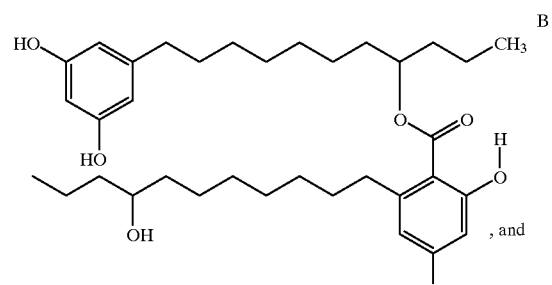

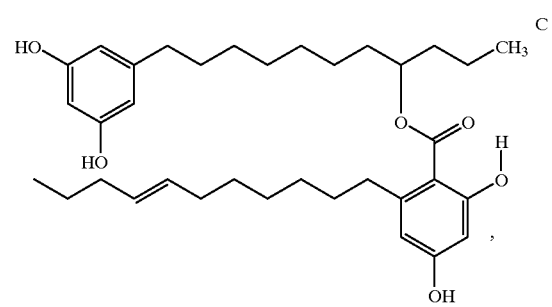

and pharmaceutically acceptable salts thereof.

Also included within the present invention are pharmaceutical compositions useful for inhibiting HIV integrase, comprising an effective amount of a compound of this invention. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:

(1) an AIDS antiviral agent,
(2) an anti-infective agent, and
(3) an immunomodulator.

This invention also discloses the culture MF6253 (ATCC 74413) identified as Cytonaema.

The present invention also relates to the preparation of compounds of structural formula I comprising:

(a) fermenting a culture of MF6253 (ATCC 74413), Cytonaema sp. or a mutant thereof to produce a fermentation broth, (b) extracting the fermentation broth with an organic solvent, (c) isolating the compounds of structural formula I.

The compounds of structural formula I are preferably isolated by partitioning the fermentation extract between the organic solvent and water, followed by size exclusion chromatography and normal or reverse-phase chromatography.

The compounds of the present invention may have asymmetric centers and may occur, except when specifically noted, as mixtures of stereoisomers or as individual diastereomers, or enantiomers, with all isomeric forms being included in the present invention.

When any variable (e.g., X, Y, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

Applicants have discovered that certain dimerized hydroxyphenylundecanes, recovered from a culture of MF6253 (ATCC 74413) identified as Cytonaema, are useful for inhibiting HIV integrase. These compounds of structural formula (I) are prepared by an aerobic fermentation procedure employing a novel culture of MF6253 (ATCC 74413) identified as Cytonaema, or a mutant thereof. A mutant refers to an organism in which some gene or the genome is modified, leaving the gene or genes responsible for the organism's ability to produce the compounds of formula (I) in recoverable amounts functional and heritable.

ATCC Deposit Cytonaema, ATCC 74413

Before the U.S. filing date of the present application, a sample of MF6253 (ATCC 74413) had been deposited at the American Type Culture Collection (ATCC), 12301 Parklawn Drive, Rockville, Md. 20852. The culture access designation is 74413. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics and Description of MF6253 (ATCC 74413)

Cytonaema sp., MF6253 (ATCC 74413) was isolated from living twigs of *Quercus ilex* collected in El Pardo, province of Madrid, Spain.

In agar culture, colonies of the fungus exhibit the following characteristics:

Colonies on oatmeal agar (DIFCO) at 23 C., 12 hr photoperiod, growing rapidly, attaining 75–78 mm diameter in 7 days, with margin even, with aerial mycelium floccose to woolly, azonate, white, with reverse dull pinkish yellow, with mycelium often collasping after a few weeks. In cultures more than 3–4 weeks old, some minute dark gray conidiomatal initias develop, but fail to mature. Odors and exudates absent.

Colonies on YME agar (DIFCO malt extract 10 g, DIFCO yeast extract 4 g, glucose 4 g, agar 20 g, 1 L $H_2O$) at 23 C., 12 hr photoperiod, growing rapidly, attaining 85–90 mm diameter in 7 days, appressed or fimbriate at the margin, raised towards the center, floccose to woolly, azonate, collasping with age, white, pale yellow in reverse. No growth at 37° C.

Colonies on cornmeal agar (DIFCO) at 23° C., 12 hr photoperiod, attaining 55–60 mm in 7 days, submerged to appressed, with scant floccose aerial mycelium, translucent to white. Exudates and odors absent.

Fertile reproductive structures were rarely observed agar culture. To reliably induce sporulation, the fungus was cultivated on wood. Four 1-cm agar plugs from YME plates were placed in a 50 mL of a dilute malt yeast extract broth (1 g malt extract, 0.5 g yeast extract, 1 L $H_2O$) with 6 strips of wood of *Robinia pseudoacacia*, approximately 4×1×0.5 cm. The broth was agitated on a gyrotary shaker (23° C., 220 rpm, 5 days) until growth was evident. Wood pieces were removed and incubated on water agar (23° C., 12 hr photoperiod, under fluorescent and near ultraviolet light). Several conidiomata were evident on wood of *Robinia pseudoacacia* after 10 days. This technique was also attempted with wood of *Betula papyrifera* and various leaf materials, but mature conidiomata were never observed.

*Conidiomata pycnidial*, superficial partly immersed in crevices, up to 700 µm in diameter, subgloblose to pyriform, papillate with a single ostiole, unilocular, solitary to confluent, dark gray to black, with scant gray mycelium extending from the conidiomatal wall. Conidomata wall a textura intricata to textura angularis, composed of densely interwoven hyphae and dark irregular plate-like cells, often with adhering vegetative hyphae.

*Conidiophores hyaline*, septate, branched at the base, acropleurogenous, forming a dense palisade that lines the conidiomatal cavity, 15–22 µm tall.

Conidiogenous cells enteroblastic, phialidic, determinate, either lateral or terminal cells, tapered towards apex, straight or curved, often with a slightly flared collarette, with periclinal thickenings sometimes evident at conidiogenous locus, up to 15 μm long×3 μm wide, arising directly from a pseudoparenchymatous layer lining the conidiomatal cavity. Conidia 4–5.5 μm×1–2 μm, cylindrical with tapered apices, allantoid or almost falcate, hyaline, smooth, aseptate, germinating on various agar media at room temperate in about 24 hrs, pale yellow in mass. Mycelium composed of highly branched, simple septate, hyaline to dematiaceous hyphae characteristic of many ascomycetous fungi.

Following the classification scheme of Sutton (Sutton, B. C. 1980. The Coelomycetes. Commonwealth Mycological Institute, Kew. U.K.), the fungus tentatively is assigned to the form genus Cytonaema based on the following combination of characteristics: stromatic, pycnidial, unilocular conidiomata; conidomata with a papillate ostiole; cylindrical, phialidic conidiogenous cells; and hyaline, allantoid or curved, aseptate conidia.

In general, MF6253 (ATCC 74413) is strain cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH of about 6–8 at the initiation and termination (harvest) of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, sucrose, dextrin, and the like. Other sources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic. cultural conditions is one method of culturing the cells. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 6–7 to the autoclaving step.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably 22–25° C., for a period of about 14–21 days, which may be varied according to fermentation conditions and scales.

Preferred culturing/production media for carrying out the fermentation those set forth in the Examples.

After growth is completed, the cells are harvested by conventional methods, e.g., centrifugation and filtration, and then extracted with the appropriate solvent, e.g., methylethylketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate is separated and concentrated to dryness initially by evaporating under reduced pressure followed by lyophilization. The compounds are finally isolated either by solvent partitioning and crystallization or by preparative HPLC on reversed phase systems.

Compounds of formula (I) may be isolated from the aerobic fermentation of a culture of MF6253 (ATCC 74413). A culture of MF6253 (ATCC 74413) is defined as substantially free of its natural soil contaminants and capable of forming compounds of structural formula (I) in recoverable amounts. The culture employed in the present invention should be free from viable contaminating microorganisms deleterious to the production of the compound of structural formula (I). A biologically pure culture of MF6253 (ATCC 74413) may also be employed.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting the free acid with a suitable organic or inorganic base.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Inteferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont | ARC |

-continued

| Drug Name | Manufacturer | Indication |
|---|---|---|
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| Indinavir | Merck (Rahway, NJ | AIDS, ARC, asymptomatic HIV positive, also in combination with AZT. |
| Nevirapine | Boeheringer Ingleheim | AIDS, ARC (protease inhibitor) |
| Delaviridine | Pharmacia-Upjohn | AIDS, ARC (protease inhibitor) |
| Ritonavir | Abbott | AIDS, ARC (protease inhibitor) |
| Saquinavir | Hoffmann-LaRoche | AIDS, ARC (protease inhibitor) |
| Nelfinavir | Agouron Pharmaceuticals | AIDS, ARC (protease inhibitor) |
| 141 W94 | Glaxo-Wellcome | AIDS, ARC (protease inhibitor) |
| DMP-266 | DuPont-Merck Pharmaceuticals | AIDS, ARC (non-nucleoside reverse transcriptase inhibitor) |
| IMMUNO-MODULATORS | | |
| AS-101 | Wyeth-Ayerst Labs (Philadelphia, PA) | AIDS |
| Bropirimine | Upjohn (Kalamazoo, MI) | advanced AIDS |
| Acemannan | Carrington Labs, Inc. (Irving, TX) | MDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS, AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999 Indinavir is generally administered at a dosage of 800 mg three times a day.

EXAMPLE 1

Fermentation
A. Media

Seed Media:

| Ingredient | grams per liter |
| --- | --- |
| corn steep liquor | 5 |
| tomato paste | 40 |
| oat flour | 100 |
| glucose | 10 |
| agar | 4 |
| $FeSO_4.7H_2O$ | 0.01 |
| $MnSO_4.4H_2O$ | 0.01 |
| $CuCl_2.2H_2O$ | 0.00025 |
| $CaCl_2$ | 0.001 |
| $H_3BO_3$ | 0.00056 |
| $(NH_4)_6Mo_7O_{24}.4H_2O$ | 0.00019 |
| $ZnSO_4.7H_2O$ | 0.002 |

The pH was adjusted to 6.8

Production media:

| Ingredient | grams per liter |
| --- | --- |
| sucrose | 75 |
| tomato paste | 10 |
| malt extract | 5.0 |
| $(NH_4)_2SO_4$ | 1.0 |
| soy flour | 1.0 |
| $KH_2PO_4$ | 9.0 |

The pH was adjusted to 7.0.

B. Inoculum Preparation

Frozen vegetative mycelia (FVM) were prepared by inoculating 50 mL of seed medium in a 250 mL flask and incubating at 25° C., 85% relative humidity and 200 rpm for 48 hours. Aliquots of the culture were frozen and used as a source of inoculum for future experiments.

C. Seed Culture

To 50 mL of seed medium in a 250 mL flask, 1.0 mL of FVM was added as inocululm and the flasks were incubated at 25° C., 85% relative humidity and 200 rpm for 48 hours.

D. Production Culture and Extraction

To 50 mL of production media in a 250 mL flask, 1.0 mL of seed culture was added as inoculum and the flasks were incubated at 25° C., 85% relative humidity and 200 rpm for 12 to 15 days. The pH of the fermentation was 4.0–4.2 at harvest. Each flask was extracted with 50 mL of methyl ethyl ketone and the solids were discarded.

EXAMPLE 2

Isolation of Compound A

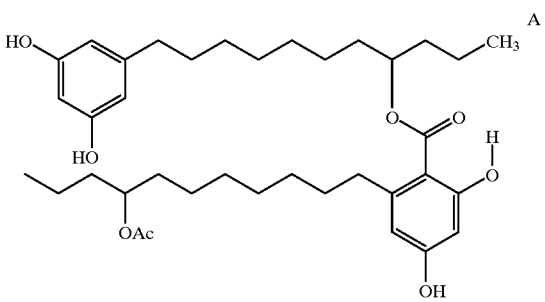

A 1.1 L whole broth of Cytonaema sp., (MF6253) was extracted with 1.0 L of methyl ethyl ketone by shaking for 30 minutes and filtered over CELITE™ diatomaceous earth. The methyl ethyl ketone layer was separated from the filtrate. The organic layer was concentrated under reduced pressure to give a mostly aqueous solution which was lyophilized to give a buff-colored material. The material was chromatographed on a 2.0 L SEPHADEX LH-20 column and eluted with methanol. The integrase activity was eluted between 2100–3300 mL of methanol eluate. The active fractions were combined and concentrated to give the semi-purified fraction. The fraction just obtained was chromatographed on a reverse phase HPLC column (ZORBAX RX C-8, 22×250 mm) eluting, at a flow rate of 10 mL per minute, with a 60 minute linear gradient of 30% to 90% of aqueous acetonitrile containing 0.1% TFA. The elution was monitored by an in-line UV detection at 230 nm. The peak eluting in between 55–61 minutes possessed all of the integrase activity. The fraction was concentrated under reduced pressure to remove most of the acetonitrile and then lyophilized to give Compound A as a gum.

EXAMPLE 3

Isolation of Compounds A, B and C

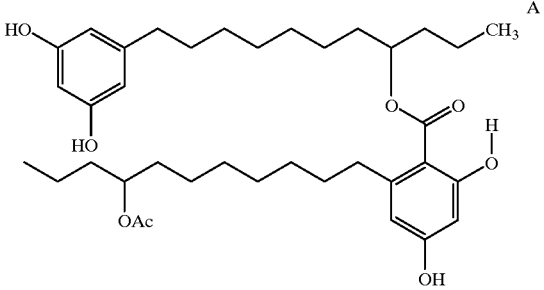

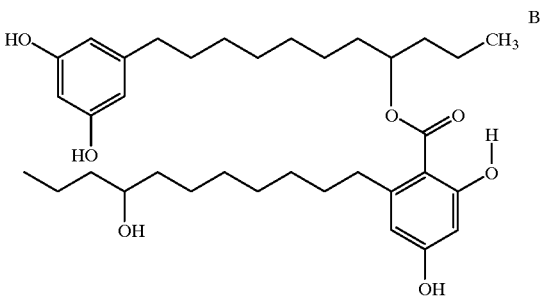

-continued

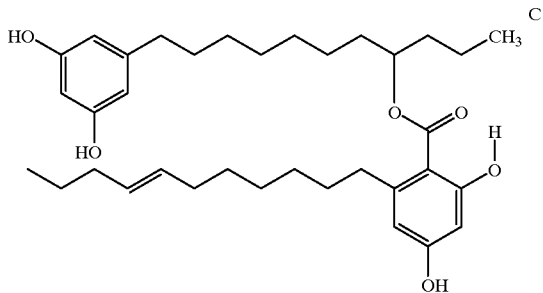

A 1.4 L whole broth of second regrowth of Cytonaema sp., MF6253 (ATCC 74413) was similarly extracted with 1.0 L of methyl ethyl ketone, as in Example 2. Processing of the extract in an identical manner gave buff-colored material. Gel filtration of one half of the material on a 2.0 L SEPHADEX LH-20 column and elution with methanol afforded the integrase activity, surprisingly, in three different zones. The fractions containing the first active zone eluted between first 2300–2500 mL of methanol, the fractions containing the second active zone eluted between 2700–2900, and the third zone eluted between 3500–5500 mL of methanol. Careful analysis of these fractions by a reverse phase analytical HPLC (ZORBAX RX C-8, 4.6×250 mm) using 80% aqueous acetonitrile containing 0.1% TFA (trifluoroacetic acid) as a mobile phase and elution at a flow rate of 1 mL per minute indicated that all three active zones contained essentially the same compounds which appeared to be more polar than compound A. The major compound eluted at 3.8 minutes and the minor compound corresponding to compound A eluted at 11 minutes. Both of these compounds had an identical UV spectra as observed by a photodiode array detector. The faster eluting compounds slowly converted in to the slower eluting compound when the fractions were left in aqueous acetonitrile containing TFA. Therefore, all three fractions obtained from LH-20 column were combined. The combined fraction was dissolved in methanol (50 mL), cooled (0° C.) and was acidified to pH 2.0 by dropwise addition of hydrochloric acid. After stirring for 10 minutes at 0° C., the mixture was concentrated to dryness and then redissolved in acetone and adsorbed over 10 g silica gel. This was then charged over a silica gel flash column (2.5×20 cm) packed in hexane. The column was washed with 15–20% ethyl acetate in hexane and eluted with 25–40% ethyl acetate in hexane to give Fraction A, Compound A and Compound B all as gums.

Fraction A (in 0.3 mL methanol) was chromatographed on a ZORBAX RX C-8 (9.4×250 mm) column and eluted with 60% aqueous acetonitrile (+0.1% TFA) for 65 minutes followed by a 10 minute gradient to 65% aqueous acetonitrile. The column was eluted at a flow rate of 4 mL/min. The fractions eluting between 84–91 minutes were combined and concentrated to remove most of the acetonitrile and then lyophilized to give Compound C as a gum.

EXAMPLE 4

Physical and Spectral Properties

I. Compound A:
  Optical rotation: [α]22D=−1o (c=0.6, MeOH)
  Ultraviolet Spectra: UV (MeOH) λmax: 208 (ε=42260), 220 (sh), 265 (15330), 301 (6908) nm
  Infra-red spectra: IR (ZnSe) νmax: 3352, 2930, 2856, 1737, 1702, 1642, 1604, 1451, 1381, 1310, 1257, 1202, 1157, 1102, 1067, 1023, 998, 928, 838, 763, 738, 713, 696 cm-1 Mass spectra: HREIMS (m/z): 628.3996 (M+, calcd. for $C_{37}H_{56}O_8$: 628.3974).
  NMR Spectra: See Table 1.

II. Compound B:
  Optical rotation: [α]22D=−5.3o (c=1, MeOH)
  Ultraviolet Spectra: UV (MeOH) λmax: 225 (ε=16924), 265 (13483), 302 (5684) nm
  Infra-red spectra: IR (ZnSe) νmax: 3333, 2930, 2856, 1702, 1604 (br), 1456, 1311, 1259, 1205, 1158, 1101, 998, 928, 839, 737, 696 cm-1; Mass spectra: HREIMS (m/z): 586.3867 (M+, calcd. for $C_{35}H_{54}O_7$: 586.3869).
  NMR Spectra: See Table 1.

III. Compound C:
  Mass spectra: HREIMS (m/z): 568.3737 (M+, calcd. for $C_{35}H_{52}O_6$: 568.3764).
  NMR Spectra: See Table 1.

$^{13}C$ NMR and $^1H$ NMR

All of the NMR spectra were recorded on a Varian Unity 400 operating at a field strength of 400 MHz for proton NMR, 100 MHz for carbon NMR respectively. The data are summarized in following Tables. The coupling constant, J, is expressed in Hz.

TABLE 1

NMR Assignments of Compound A and Compound B in CD₃CN at 400 MHz

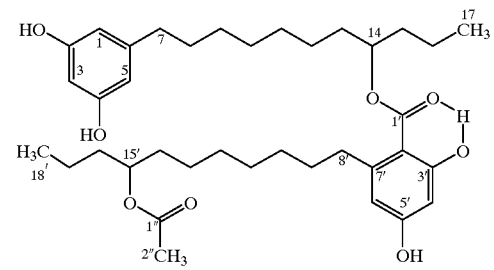

| Position | compound A δC | compound B δC | compound A δH, mult, J in Hz | compound B δH, mult, J in Hz | compound C* δH, mult, J in Hz |
|---|---|---|---|---|---|
| 1 | 108.0 | 108.0 | 6.12, d, 2.4 | 6.13, d, 2.4 | 5.98, d, 2.0 |
| 2 | 158.9 | 158.9 | — | — | — |
| 3 | 100.7 | 100.7 | 6.06, t, 2.4 | 6.05, t, 2.4 | 5.94, t, 2.4 |
| 4 | 158.9 | 158.9 | — | — | — |
| 5 | 108.0 | 108.0 | 6.12, d, 2.4 | 6.13, d, 2.4 | 5.98, d, 2.0 |
| 6 | 146.6 | 146.5 | — | — | — |
| 7 | 36.5 | 36.5 | 2.40, t, 8.0 | 2.40, t, 8.0 | 2.27, t, 8.0 |
| 8 | 32.01 | 32.04 | 1.50, m | 1.50, m | 1.37, m |
| 9 | 29.96 | 30.00 | 1.22, m | 1.22, m | 1.14, m |
| 10 | 30.06ᵃ | 30.09ᵃ | 1.22, m | 1.22, m | 1.14, m |
| 11 | 30.19ᵃ | 30.25ᵃ | 1.22, m | 1.22, m | 1.14, m |
| 12 | 26.3 | 26.3 | 1.22, m | 1.22, m | 1.14, m |
| 13 | 35.0 | 35.0 | 1.65, m | 1.65, m | 1.50, m |
| 14 | 76.8 | 76.81 | 5.21, pent, 6.0 | 5.21, pent, 6.4 | 5.07, m |
| 15 | 37.24 | 37.23 | 1.62, m | 1.62, m | 1.50, m |
| 16 | 19.7 | 19.71 | 1.30, m | 1.30, m | 1.14, m |
| 17 | 14.3 | 14.4 | 0.87, t, 6.8 | 0.87, t, 6.8 | 0.78, t, 7.2 |
| 1' | 172.5 | 172.49 | — | — | — |
| 2' | 105.5 | 105.5 | — | — | — |
| 3' | 166.3 | 166.3 | — | — | — |
| 4' | 101.9 | 101.9 | 6.19, d, 2.4 | 6.19, d, 2.4 | 6.04, d, 2.4 |
| 5' | 162.8 | 162.8 | — | — | — |
| 6' | 111.8 | 111.8 | 6.23, d, 2.4 | 6.23, d, 2.4 | 6.04, d, 2.4 |
| 7' | 148.7 | 149.69 | — | — | — |
| 8' | 37.6 | 37.6 | 2.78, m | 2.81, m | 2.67, t, 8.8 |
| 9' | 33.2 | 33.3 | 1.50, m | 1.50, m | 1.37, m |
| 10' | 30.7 | 30.80 | 1.22, m | 1.22, m | 1.14, m |
| 11' | 30.38ᵃ | 30.58ᵃ | 1.22, m | 1.22, m | 1.14, m |
| 12' | 30.28ᵃ | 30.61ᵃ | 1.22, m | 1.22, m | 1.14, m |
| 13' | 26.1 | 26.6 | 1.22, m | 1.22, m | 1.84, m |

TABLE 1-continued

NMR Assignments of Compound A and Compound B in CD$_3$CN at 400 MHz

| Position | compound A δC | compound B δC | compound A δH, mult, J in Hz | compound B δH, mult, J in Hz | compound C* δH, mult, J in Hz |
|---|---|---|---|---|---|
| 14' | 35.0 | 35.0 | 1.45, m | 1.45, m | 5.28, dt, 15.2, 5.6 |
| 15' | 74.6 | 71.8 | 4.82, pent, 6.4 | 3.49, m | 5.22 dt, 15.2, 5.6 |
| 16' | 37.19 | 38.32 | 1.45, m | 1.45, m | 1.84, m |
| 17' | 19.4 | 19.64 | 1.35, m | 1.35, m | 1.14, m |
| 18' | 14.3 | 14.6 | 0.90, t, 7.2 | 0.90, t, 7.2 | 0.80, t, 7.2 |
| 1" | 171.48 | — | — | — | — |
| 2" | 21.4 | — | 1.95, s | — | — |
| 3'-OH | — | — | 11.76, s | 11.77, s | 11.77, s |
| 3xOH | — | — | 6.8, brs | 7.08, brs | 6.27, 7.14, brs |

$^a$chemical shifts could be interchanged.
*spectrum recorded in a mixture of CD$_3$CN + CDCl$_3$.

EXAMPLE 5

Preparation of Compound B by Acidic Hydrolysis of Compound A

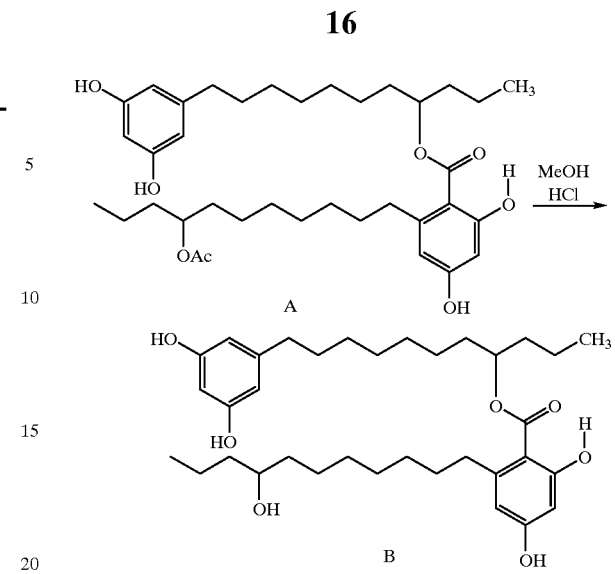

To a solution of compound A (2.2 mg) in methanol (0.5 mL) was added 0.05 mL conc. hydrochloric acid and the solution was allowed to stand at room temperature. The rate of the hydrolysis was monitored by reverse phase analytical HPLC (ZORBAX RX C-8, 4.6×250 mm, 80% aqueous acetonitrile +0.1% TFA, 1 mL/min). The appearance of a peak at $t_R$ 7 minute was observed at the expense of the starting material ($t_R$ 10 min). After 48 hrs, when most of the starting material was used up, the reaction mixture was concentrated by a stream of nitrogen. The product was purified on a Pasteur pipette filled with silica gel and eluted with 20–30% ethyl acetate in hexane to give Compound B as a gum.

EXAMPLE 6

Preparation of Compound D by Basic Hydrolysis of Compound B

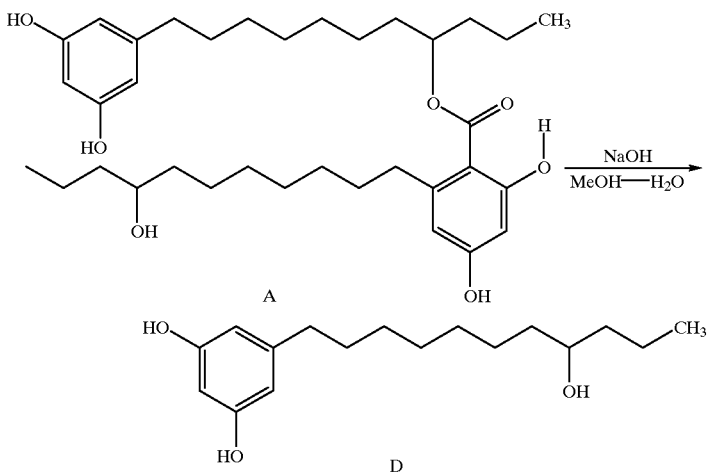

To a solution of Compound B in a 3:2 mixture of methanol-water (5 mL) was added 4N sodium hydroxide solution (1.5 mL stirred at room temperature overnight. Since no reaction was observed, the mixture was heated at reflux for 6 hrs. Reaction was complete and a single product ($t_R$ 3 min) was formed as indicated by a reverse phase analytical HPLC (ZORBAX RX C-8, 4.6×250 mm, 80% aqueous acetonitrile +0.1% TFA, 1 mL/min). After complete disappearance of the starting material, the reaction mixture was diluted with water and cooled to 0° C. and acidified to pH 2.0 by addition of hydrochloric acid. The mixture was extracted with ethyl acetate (3×20 mL), washed twice with water, dried over sodium sulfate, concentrated under reduced pressure to dryness and chromatographed on a reverse phase HPLC column (ZORBAX RX C-8, 22×250 mm) using a 60 minute linear gradient of 10% to 90% aqueous acetonitrile +0.1% TFA. The column was eluted at a flow rate of 10 mL/min to elute the product between 37 and 43 minutes. The product fractions were concentrated under reduced pressure and then lyophilized to give homogeneous Compound D as a gum.

$[\alpha]22D=-2.9o$ (c=0.28, MeOH); UV (MeOH) λmax: 208 (ε=13180), 274 (1560) nm; IR (ZnSe) vmax: 3289, 2929, 2856, 1602, 1511, 1466, 1340, 1205, 1148, 998, 840, 7257, 696 cm-1; $^1$H NMR (CDCl$_3$+CD$_3$CN) δ: 0.75 (3H, app t, J=6.4 Hz), 1.14–1.24 (14H, m), 1.39 (2H, m), 2.28 (2H, t, J=8 Hz), 3.39 (1H, brs, CHOH), 5.94 (1H, s, ArH), 5.99 (2H, brs, ArH); $^{13}$C NMR (CDCl$_3$+CD$_3$CN) δ: 13.91 (CH$_3$), 18.68, 25.41, 28.93, 29.20, 29.42, 30.91, 35.60, 37.30, 39.54 (all CH$_2$), 71.08 (CH), 99.85 (CH), 107.08 (2×CH), 145.27 (C$^o$), 157.45 (2×C$^o$); HREIMS (m/z): 280.0235 (M$^+$, calcd. for C$_{17}$H$_{28}$O$_3$: 280.2038).

EXAMPLE 7

HIV Integrase Substrate Cleavage

As assay for endonucleolytic processing and joining of the 3' end of HIV long terminal repeat terminus by HIV-1 integrase was conducted according to Hazuda, et al., Nud. Acids Res., 22, 1121 (1994), herein incorporated by reference for these purposes. To assay inhibition of the coupled reaction, the assay was conducted with inhibitor having various concentrations in the range of 1 to 100 μM. Results follow:

| Compound | IC$_{50}$ (μm) |
|---|---|
| A | 3.2 |
| B | 6.1 |
| C | 3.5 |
| D | 93 |

EXAMPLE 8

Strand Transfer Assay for HIV Integrase

A microtiter assay for strand transfer of processed donor (HIV) DNA to nonspecific, nicked target DNA was conducted according to Wolfe, et al., J. Virol., 70, 1424 (1996), herein incorporated by reference for these purposes. To assay inhibition of such strand transfer by HIV integrase, the reaction was conducted with inhibitor having various concentrations in the range of 1 to 100 μM. Results follow:

| Compound | IC$_{50}$ (μM) |
|---|---|
| A | 32 |
| B | 17 |
| C | >88 |
| D | >100 |

EXAMPLE 9

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:

1. A compound of the formula

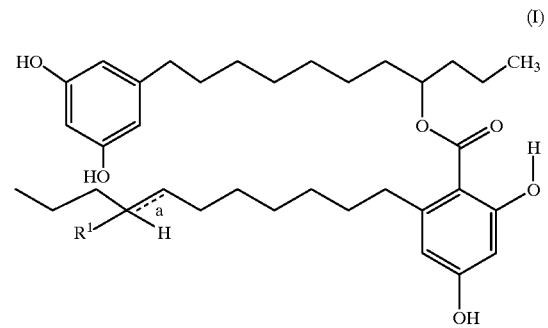

wherein:
when "a" represents a single bond, R$^1$ is selected from:
(1) —OH, and
(2) —OC(O)—CH$_3$; and
when "a" represents a double bond,
R$^1$ is absent,
and pharmaceutically acceptable salts and esters thereof.

2. The compound according to claim 1 selected from:

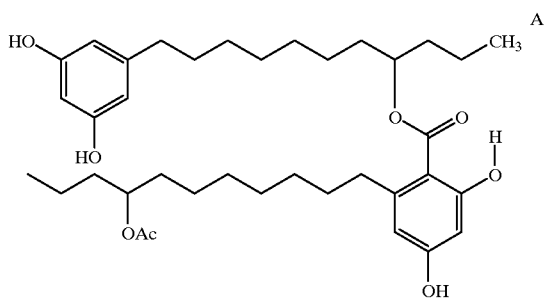

-continued

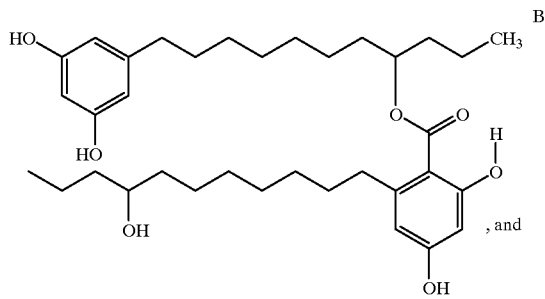

, and

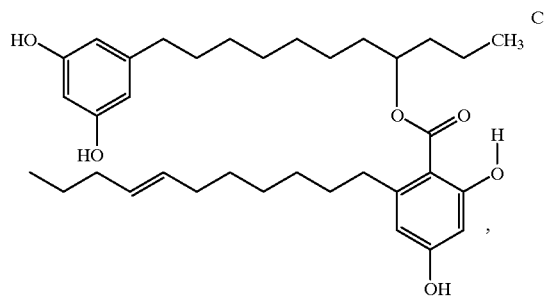

or a pharmaceutically acceptable salt thereof.

3. The compound of claim 1 of formula (A):

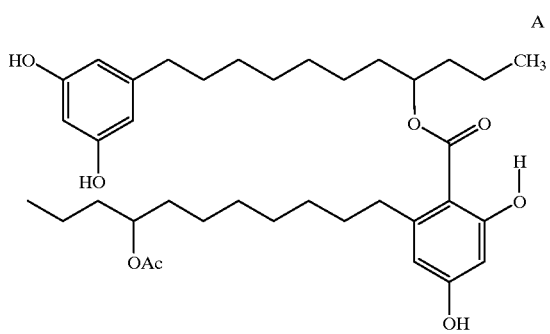

or a pharmaceutically acceptable salt thereof.

4. The compound of claim 1 of formula (B):

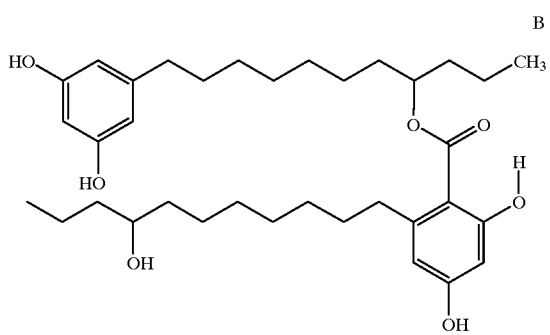

or a pharmaceutically acceptable salt thereof.

5. The compound of claim 1 of formula (C):

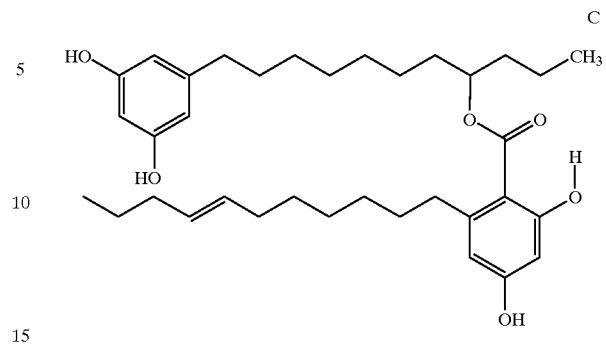

or a pharmaceutically acceptable salt thereof.

6. A pharmaceutical composition useful for inhibiting HIV integrase, comprising an effective amount of the compound according to claim 1.

7. The pharmaceutical composition of claim 6, useful for treating infection by HIV, or for treating AIDS or ARC.

8. A pharmaceutical composition comprising a therapeutically effective amount of a compound of claim 1 in combination with a therapeutically effective amount of an AIDS treatment agent selected from:

(1) an AIDS antiviral agent, (2) an anti-infective agent, and (3) an immunomodulator.

9. The composition of claim 8 wherein the antiviral agent is an HIV protease inhibitor.

10. The composition of claim 9 wherein the HIV protease inhibitor is N-(2(R)-hydroxy-1-(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof.

11. A pharmaceutical composition made by combining the compound of claim 1 and a pharmaceutically acceptable carrier.

12. A process for making a pharmaceutical composition comprising combining a compound of claim 1 and a pharmaceutically acceptable carrier.

13. A method of inhibiting HIV integrase, comprising the administration to a mammal in need of such treatment of a therapeutically effective amount of a compound of claim 1.

14. A method of treating infection by HIV, or of treating AIDS or ARC, comprising administration to a mammal in need of such treatment of a therapeutically effective amount of a compound of claim 1.

* * * * *